(12) United States Patent
Trombley, III et al.

(10) Patent No.: US 7,060,049 B2
(45) Date of Patent: Jun. 13, 2006

(54) INJECTION SYSTEM HAVING AN AGITATION MECHANISM FOR CIRCULATING A FLUID MEDIUM

(75) Inventors: Frederick W. Trombley, III, Gibsonia, PA (US); Arthur E. Uber, III, Pittsburgh, PA (US); Edward J. Rhinehart, Monroeville, PA (US); Rosemary Almon-Martin, Saxonburg, PA (US); Alan D. Hirschman, Glenshaw, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 10/435,802

(22) Filed: May 12, 2003

(65) Prior Publication Data

US 2003/0195463 A1      Oct. 16, 2003

Related U.S. Application Data

(62) Division of application No. 09/267,237, filed on Mar. 12, 1999, now Pat. No. 6,575,930.

(51) Int. Cl.
*A61M 37/00* (2006.01)

(52) U.S. Cl. .................. 604/82; 604/131; 239/142; 366/165.4

(58) Field of Classification Search .............. 604/6.11, 604/19, 518, 519, 82–92, 131–155, 181, 604/187, 207
See application file for complete search history.

(56) References Cited

U.S. PATENT DOCUMENTS

| | | | |
|---|---|---|---|
| 2,660,171 A | 11/1953 | Dickinson, Jr. | |
| 2,724,383 A | 11/1955 | Lockhart | |
| 3,397,694 A | 8/1968 | Ogle | |
| 3,604,417 A | 9/1971 | Stolzenberg | |
| 3,789,670 A | 2/1974 | Rosenwald | |
| 3,831,903 A | 8/1974 | Harmel, Jr. | |

(Continued)

FOREIGN PATENT DOCUMENTS

DE            34 11 427          10/1985

(Continued)

OTHER PUBLICATIONS

International Search Report for PCT Application No. PCT/US00/06367.

(Continued)

*Primary Examiner*—Glenn K. Dawson
(74) *Attorney, Agent, or Firm*—Gregory L. Bradley; Henry E. Bartoney, Jr.

(57) ABSTRACT

A system for dispensing a medium includes at least a first container to hold the medium, a pressurizing device, such as a pump, in fluid connection with the container for pressurizing the medium, and an agitation mechanism or device to maintain the components of the medium in a mixed state. The container and the pressurizing device can be separate units, as in the case of an bag or bottle in fluid connection with a peristaltic or other type of pump. The container and the pump can also be combined in a single unit, as in the case of a syringe, wherein the syringe barrel of the syringe acts to contain the medium and the syringe plunger pressurizes the medium within the syringe barrel. A method of injecting a multi-component medium includes the step of agitating the medium (for example, as described above) before or during an injection procedure to maintain the components of the medium in a mixed state.

16 Claims, 16 Drawing Sheets

U.S. PATENT DOCUMENTS

| | | | |
|---|---|---|---|
| 3,880,138 A | 4/1975 | Wootten et al. | |
| 3,930,492 A | 1/1976 | Hatsuno et al. | |
| 4,008,718 A | 2/1977 | Pitesky | |
| 4,172,457 A | 10/1979 | Choksi et al. | |
| 4,417,861 A * | 11/1983 | Tolbert | 417/315 |
| 4,687,000 A | 8/1987 | Eisenhardt et al. | |
| 4,784,297 A | 11/1988 | Katz | |
| 4,846,786 A | 7/1989 | Freed et al. | |
| 4,872,353 A * | 10/1989 | Orr et al. | 73/864.85 |
| 5,240,322 A | 8/1993 | Haber et al. | |
| 5,352,036 A | 10/1994 | Haber et al. | |
| 5,360,410 A | 11/1994 | Wacks | |
| 5,383,858 A | 1/1995 | Reilly et al. | |
| 5,401,253 A | 3/1995 | Reynolds | |
| 5,425,580 A | 6/1995 | Beller | |
| 5,469,849 A | 11/1995 | Sasaki et al. | |
| 5,528,923 A | 6/1996 | Ledez et al. | |
| 5,601,086 A | 2/1997 | Pretlow, III et al. | |
| 5,611,344 A | 3/1997 | Bernstein et al. | |
| 5,686,060 A | 11/1997 | Schneider et al. | |
| 5,783,254 A | 7/1998 | Maynard | |
| 5,806,519 A | 9/1998 | Evans, III et al. | |
| 5,840,026 A | 11/1998 | Uber, III et al. | |
| 5,846,517 A | 12/1998 | Unger | |
| 6,317,623 B1 | 11/2001 | Griffiths et al. | |
| 2002/0077588 A1 | 6/2002 | Schneider et al. | |
| 2003/0199815 A1 | 10/2003 | Trombley, III et al. | |

FOREIGN PATENT DOCUMENTS

| | | |
|---|---|---|
| DE | 39 34 024 | 4/1991 |
| DE | 296 22 313 | 4/1997 |
| DE | 196 25 102 | 8/1997 |
| EP | 0 033 292 | 8/1981 |
| EP | 0 770 352 | 5/1997 |
| WO | WO 96/18420 | 6/1996 |
| WO | WO 97/18845 | 5/1997 |
| WO | WO 98/22168 | 5/1998 |
| WO | WO 98/33538 | 8/1998 |
| WO | WO 99/27981 | 6/1999 |
| WO | WO 00/12157 | 9/2000 |
| WO | WO 00/12158 | 9/2000 |
| WO | WO 00/53242 | 9/2000 |

OTHER PUBLICATIONS

"A Particulate Contrast Agent With Potential for Ultrasound Imaging of the Liver," Ultrasound in Med. & Biol., vol. 13, No. 9, pp. 555-556 (1987).

"Selective Destruction of Contrast Agent Microspheres," Bouakaz et al., IEEE Ultrasonics Symposium, pp. 1693-1696 (1999).

"Effect of Ultrasound on the Release of Micro-Encapsulated Drugs," Frinking et al., Ultrasonics 36, pp. 709-712 (1998).

* cited by examiner

INJECTION SYSTEM HAVING AN AGITATION MECHANISM FOR CIRCULATING A FLUID MEDIUM

CROSS-REFERENCE TO RELATED APPLICATION

This application is a divisional of application Ser. No. 09/267,237, filed on Mar. 12, 1999, now U.S. Pat. No. 6,575,930, the contents of which are hereby incorporated by reference.

BACKGROUND OF THE INVENTION

The present invention relates generally to agitation devices and dispensing systems incorporating such agitation devices, and, more particularly, to agitation devices and dispensing systems (for example, injection systems) for use in connection with delivery of a multi-component medium to a patient.

In a number of medical procedures, it is desirable to inject a multi-component injection medium into a patient. An example of such a medical procedure is ultrasound imaging.

Ultrasound imaging creates images of the inside of the human body by broadcasting ultrasonic energy into the body and analyzing the reflected ultrasound energy. Differences in reflected energy (for example, amplitude or frequency) appear as differences in gray scale or color on the output images. As with other medical imaging procedures, contrast-enhancing fluids (often referred to as contrast media) can be injected into the body to increase the difference in the reflected energy and thereby increase the gray scale or color contrast displayed in the image (that is, the image contrast) viewed by the operator.

For ultrasonic imaging, the most common contrast media contain many small bubbles. The difference in density of bubbles when compared to water, and thus their difference in sound transmission, makes small gas bubbles excellent means for scattering ultrasound energy. Small solid particles can also serve to scatter ultrasonic energy. Such particles are typically on the order of 1 to 10 microns (that is, $10^{-6}$ to $10^{-5}$ meters) in diameter. These small particles can pass safely through the vascular bed.

Contrast media suitable for use in ultrasound are supplied in a number of forms. Some of these contrast media are powders to which liquid is added just before use. The powder particles cause a gas bubble to coalesce around them. The powder must be mixed with a liquid, and the mixture must be agitated with just the right amount of vigor to obtain the optimum creation of bubbles. Another type of contrast medium is a liquid that is agitated vigorously with air. There are no solid particles to act as nuclei, but the liquid is a mixture of several liquid components that make relatively stable small bubbles. A third type of contrast medium uses "hard" spheres filled with a gas. These contrast media are typically supplied as a powder that is mixed with a liquid. The goal is to suspend the spheres in the liquid without breaking them. Even though such spheres have a shell that is hard compared to a liquid, they are very small and relatively fragile. It is also possible for the solid particles themselves to act to scatter ultrasonic energy, but the acoustical properties of the solid spheres are not as different from water as those of a gas so the difference in reflected energy is not as dramatic.

Contrast medium particles also enhance other modes of ultrasonic imaging. For example, when the particles are carried along in the blood stream, the reflected energy is Doppler shifted. This Doppler shift allows an estimation of the speed of blood flow. Bubbles can also be excited so that they radiate ultrasonic energy at the second harmonic of the incident ultrasonic energy. This harmonic imaging is dependent upon the non-linearity of the reflectors. Gas bubbles work well as harmonic reflectors.

After mixing/preparation as described above, the contrast medium is drawn into a syringe or other container for injection into the patient. Typically, the fluid is injected into the vein in the arm of the patient. The blood dilutes and carries the contrast medium throughout the body, including to the area (i.e., the region-of-interest or ROI) of the body being imaged.

It is becoming more common for a microprocessor controlled power injector to be used for injecting the contrast medium. Compared to a hand injection of contrast, this has the benefit of maintaining a consistent flow over a long time, thereby providing a consistent amount of contrast medium (number of particles) in the blood stream. If there are too few particles, for example, there is insufficient image contrast and the diagnosis cannot adequately be made. If too many particles are present, too much energy is reflected, resulting in blooming or saturation of the ultrasound receiver.

Although a power injector can inject contrast medium at a constant flow rate, there must be a constant number of bubbles per volume of fluid injected to provide a constant image contrast. Because a gas is significantly less dense than water and other liquids, however, gas bubbles will rise in a liquid. The rate of rise is related to the diameter of the gas bubble. This density difference provides a useful tool to quickly separate large bubbles created during the initial mixing. However, the small bubbles desired for image enhancement will also rise slowly. Solid particles, on the other hand, will tend to settle or sink because most solids are more dense than water. Many minutes can elapse between the initial mixing of the contrast medium and the injection into the patient, and/or the injection itself may be several minutes in duration. If the concentration of particles changes, the image contrast may be degraded.

It is, therefore, very desirable to develop systems and methods to maintain multi-component contrast media in a mixed state throughout an injection proceeding.

SUMMARY OF THE INVENTION

The present invention provides devices, systems and methods for dispensing a multi-component medium (for example, an ultrasound contrast medium) via injection into a patient. Such a system includes generally at least a first container to hold the medium, a pressurizing device, such as a pump, in fluid connection with the container for pressurizing the medium, and an agitation mechanism or device to maintain the components of the medium in a mixed state. The container and the pressurizing device can be separate units, as in the case of an bag or bottle in fluid connection with a peristaltic or other type of pump. The container and the pump can also be combined as a single unit, as in the case of a syringe, wherein the syringe barrel of the syringe acts to contain the medium and the syringe plunger pressurizes the medium within the syringe barrel.

The contrast media with which this invention operates optimally contain contrast enhancement agents which interact with the energy beamed into the body for creation of the image. The energy can be ultrasonic or electromagnetic. Common electromagnetic energies include X-rays and light. The contrast enhancement agents include but are not limited to microbubbles—with or without a solid core or nucleus, microspheres with relatively rigid shells filled with gas or liquid, liposomes with relatively flexible shells filled with gas or liquid, solid micro-particles, or microspheres of a liquid that is not miscible with the liquid in the contrast media. Any contrast media involving two immiscible materials or different phases of material could benefit from this invention. Contrast media where the molecules of the contrast enhancing material dissolve in the liquid of the contrast media can benefit from this invention to the extent that they are mixed from two different phases or to the extent that they might separate during storage or use.

In one embodiment, the agitation mechanism operates by inducing bulk motion of the first container. In this embodiment, free moving or fixed objects may be placed within the container to assist in mixing. The agitation mechanism may, for example, rotate or shake randomly the first container about a point.

The agitation mechanism may also rotate the first container about at least one axis of the container. In this embodiment, the first container may be formed asymmetrically about the axis to reduce the effects of rotational symmetry. The first container may also include a fixed or movable flow member therein to reduce the effects of rotational symmetry about the axis.

In another embodiment, the agitation mechanism induces currents within the medium without bulk motion of the container. For example, the agitation mechanism may include a movable stirring member within the first container. Moreover, convection currents may be induced in the medium by heating. Ultrasonic energy can also used to induce currents within the medium. Likewise, electromagnetic energy can be used to induce currents within the medium when the medium is electrically conductive.

A gas may also be released into the medium to induce currents therein. Preferably, such a gas is sterile and biologically inactive.

In the case that the first container is compressible, the agitation mechanism can operate to compress the first container to induce mixing. For example, the agitation mechanism can include a roller that moves over the first container. Alternatively, the agitation mechanism can compress alternating sections of the first container.

In still another embodiment, the system can operate to circulate the fluid with an agitation pump. The agitation pump and the injection pressurization pump can be the same or different units. Such a system can, for example, include a second container, and the agitation pump can operate to move at least a portion of the medium between the first container and the second container. The medium may be moved between the first container and the second container in an alternating fashion.

The present invention also provides a method of dispensing a multi-component medium. The method includes the step of agitating the medium (for example, as described above) before or during an injection procedure to maintain the components of the medium in a mixed state. As used herein, the phrase "during an injection procedure" refers generally to the time after initial preparation or mixing of the contrast medium through completion of the injection into the patient. The step of agitating the medium can be accomplished as described above.

The present invention, together with its attendant advantages, will be further understood by reference to the following detailed description and the accompanying drawings.

DETAILED DESCRIPTION OF THE INVENTION

In several embodiments, the present invention provides a number of devices, systems and methods to facilitate or to improve the initial creation and/or mixing of contrast medium, and to agitate the contrast medium to maintain a relatively uniform distribution of the contrast enhancing agent or particles throughout the liquid contrast medium prior to and/or during an injection procedure. The present invention is applicable generally to multi-component fluids wherein the components are not totally miscible and there is a tendency for the components to separate over time. The present invention is also applicable to miscible or dissolvable materials during the initial preparation phase when a uniform mixture has not yet been created.

The agitation mechanisms or devices of the present invention can be categorized broadly into three classes, which can be used separately or in combination. In the first class of agitation mechanism, the contrast medium is agitated by bulk movement of the entire storage volume or container in which the contrast medium is prepared and/or kept prior to and/or during injection into the patient. The second class of agitation mechanism agitates the contrast medium within the storage volume or container without bulk movement of the storage volume or container. The third class of agitation mechanism agitates the contrast medium by circulating/transporting the contrast medium using an agitation pump. For example, the contrast medium can be transported between two storage volumes or containers in an alternating manner. In most cases, the agitation systems of the present invention can be easily adapted to perform the initial combination/mixing/preparation of the powder and liquid components of a medium.

Figure 1A:
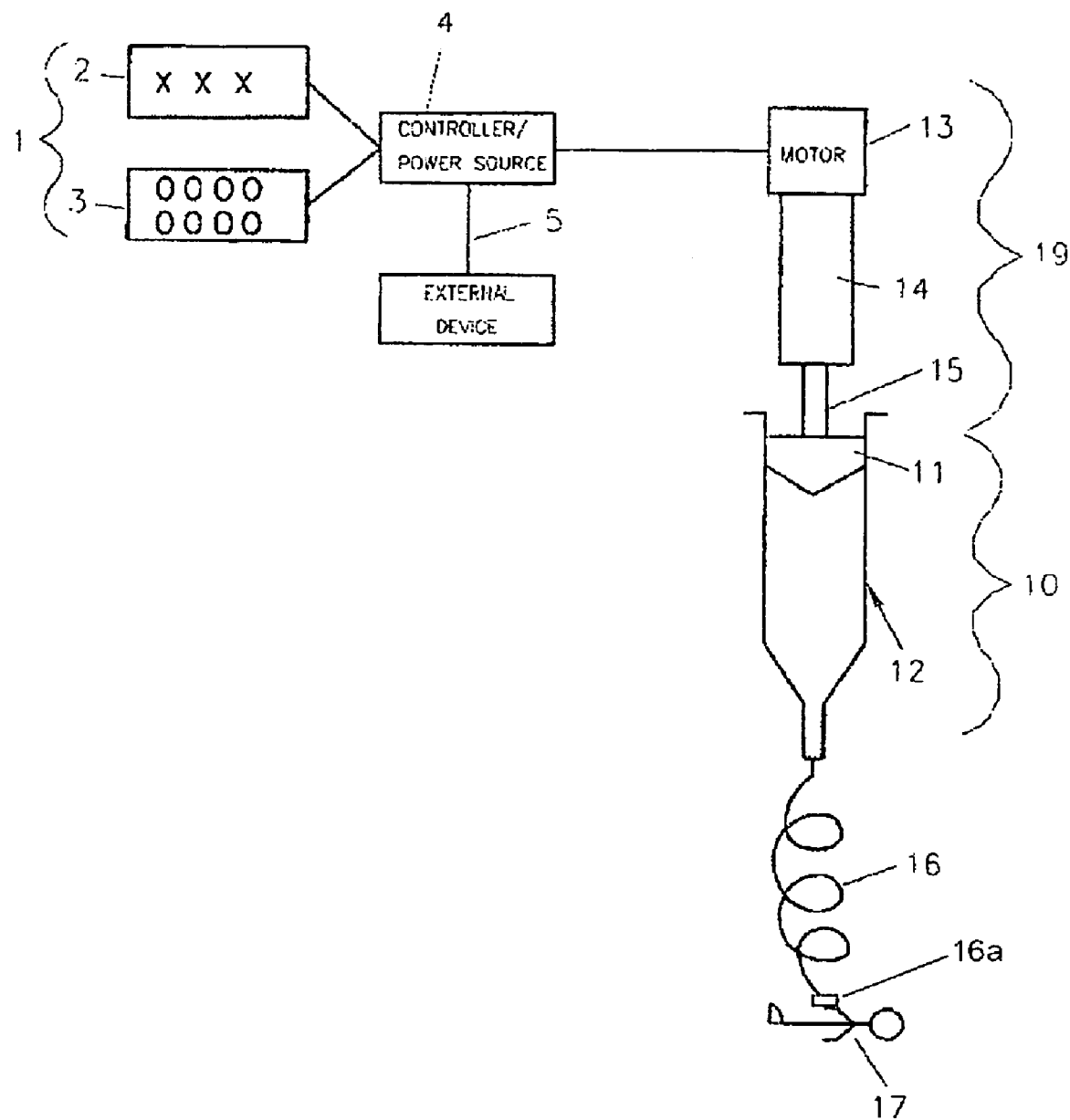
FIG. 1A illustrates an embodiment of an dispensing system.
Figure 1B:
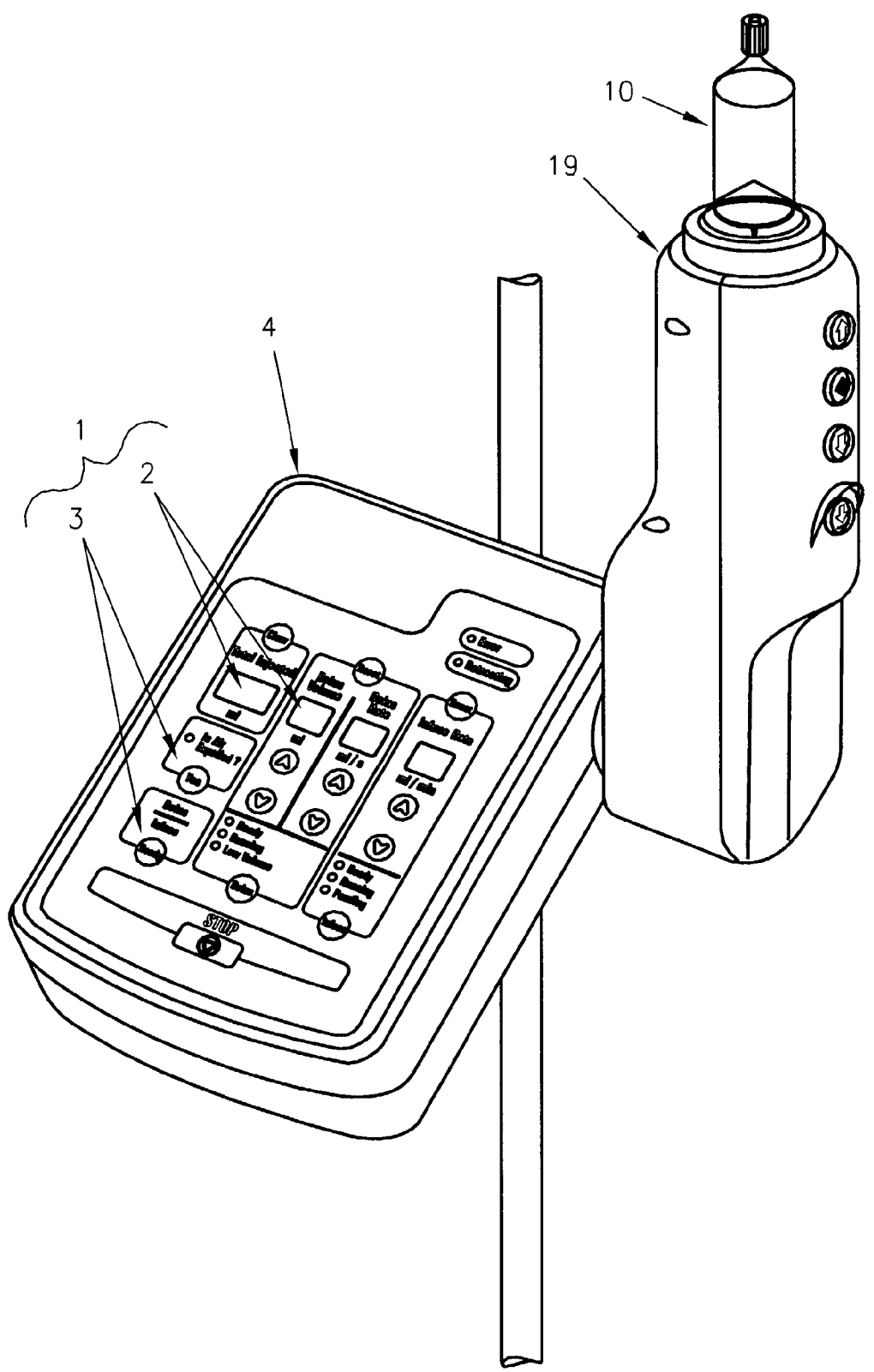
FIG. 1B illustrate another embodiment of an dispensing system.
Figure 2:
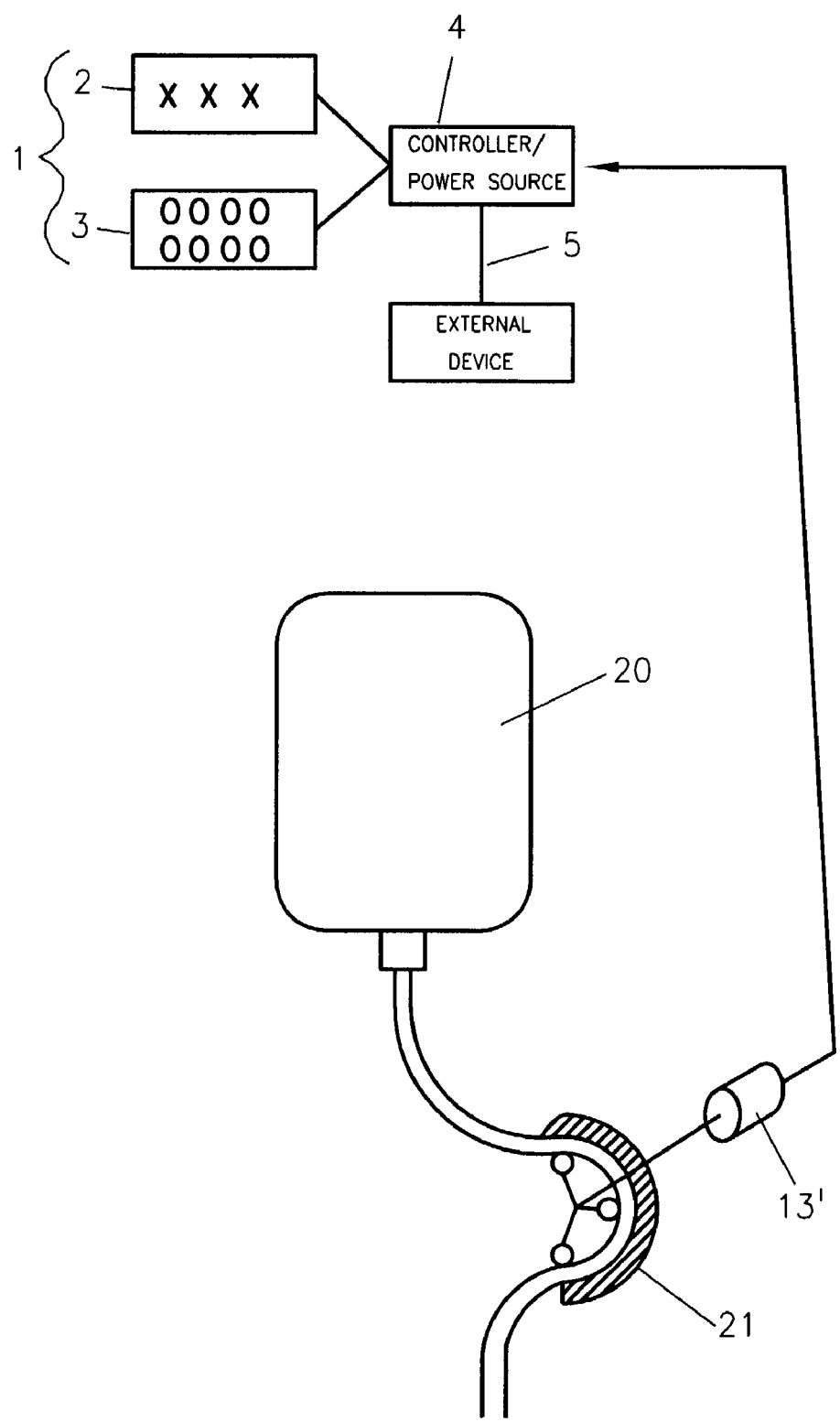
FIG. 2 illustrates yet another embodiment of an dispensing system.

FIGS. 1A, 1B and 2 illustrate examples of powered injector systems in which the agitation mechanisms or devices of the present invention can be incorporated. In general, such injector systems typically include a user interface, a controller/power source, a contrast medium storage volume, and a pressurizing device, such as a pump.

In the syringe-based injector shown in FIG. 1A, the contrast medium storage volume and pressurizing device are combined in syringe 10. In that regard, the contrast medium is contained in syringe barrel 12 and is pressurized within barrel 12 by plunger 11, as known in the art. Plunger 11 slides within barrel 12 to draw in and expel the contrast medium.

The injector system further includes a motor 13 and a mechanical assembly 14 that changes rotational motion to linear motion to push piston 15 against syringe plunger 11 within syringe 10. A mounting mechanism (not shown), such as is described in U.S. Pat. No. 5,383,858, may be used to mount syringe 10 in a fixed position.

A user interface 1 includes a device 3 for input of data (for example, a keyboard) and a display 2. User interface 1 is also preferably in communicative connection with a feedback/alarm system (not shown). User interface 1 preferably connects to a controller/power source 4 to enable the user to program the parameters of an injection and to control an injection. The user can also directly control mixing and agitation of the contrast medium as described herein without use of a controller 4.

To complete the components of the injection system, a connector tube 16, terminating in a patient interface 16a, carries the contrast medium from syringe 10 to a patient 17. As commonly practiced, large bubbles are preferably removed from the fluid path before connecting to the patient.

FIG. 1B illustrates an embodiment of a commercially available ultrasound contrast medium injector, namely the MEDRAD PULSAR™ injector system marketed by Medrad, Inc., the assignee of the present application. The reference numbers defined in connection with FIG. 1A indicate the location of corresponding elements in FIG. 1B, although not all the elements are visible.

In an alternative injector embodiment shown in FIG. 2, a container 20, such as a bag, acts as the contrast medium storage volume. A motor 13' and a peristaltic pump 21 cooperate to pressurize the injection fluid. User interface 1 and controller/power source 4 serve the same function as described in relation to FIGS. 1A and 1B.

The agitation devices and systems disclosed herein can be used with many injectors and injector systems other than set forth in FIGS. 1A, 1B and 2. For example, a simple spring-powered syringe pump that runs at a constant rate can be used as an injector. The user interface may, for example, have only start and stop capabilities. Indeed, an external source of power is not required. In that regard, a person could be part of the contrast injector system and perform many of the functions described above. A person, for example, can manually operate a syringe. Mechanical injectors, however, are better able to perform injections consistently and precisely.

As discussed above, the first category of agitation devices of the present invention operate by inducing gross or bulk motion of the contrast medium storage volume. The most basic strategy is to move, rotate, or rock the contrast medium storage volume. This manner of agitation is relatively simple, for example, with a bag connected via a tube to a peristaltic pump.

Figure 3A:
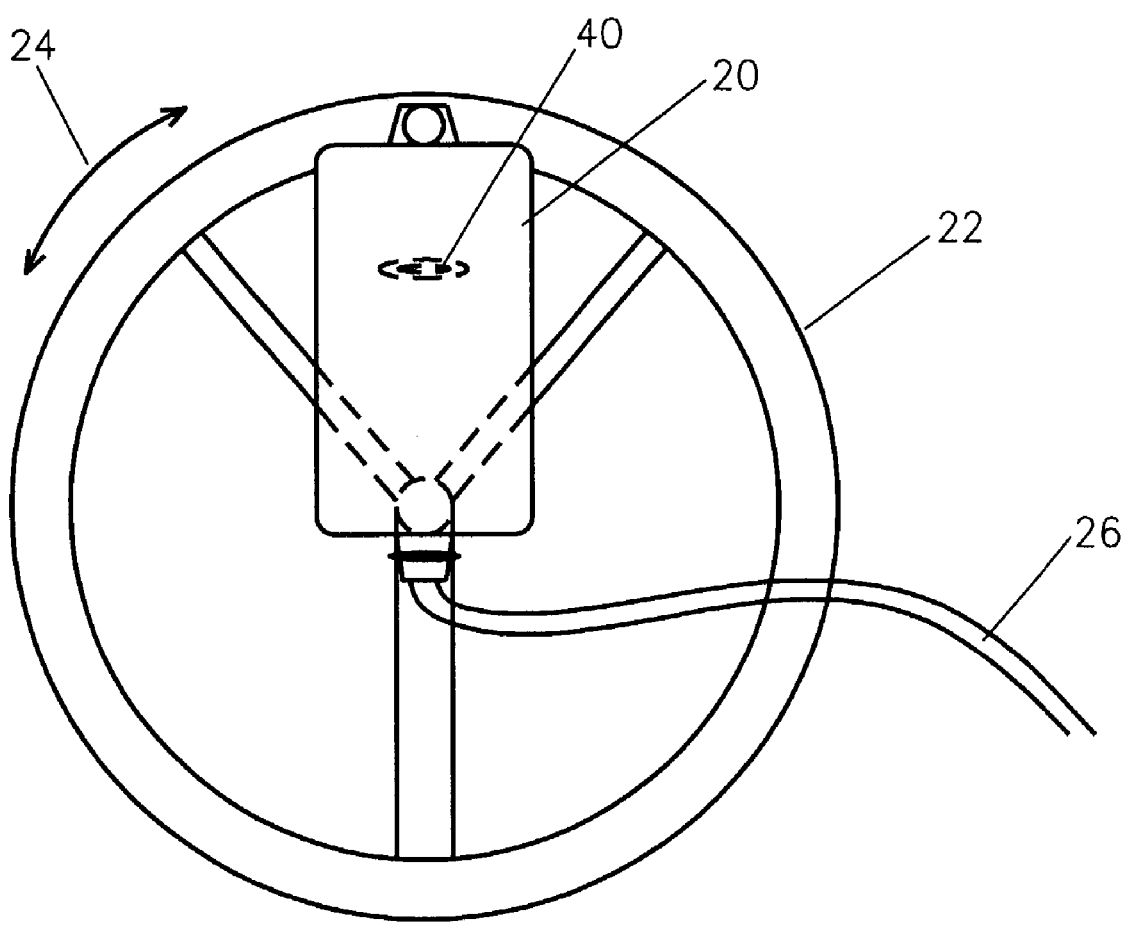
FIG. 3A illustrates an embodiment of an agitation mechanism for a contrast container.

In general, a simple reciprocating bag holder 22 as shown in FIG. 3A will suffice. In this embodiment, a bag 20 is attached to a bag holder 22. To simplify the mechanics, the rotation may be reciprocal as indicated by arrow 24. The rotation of bag holder 22 can be made continuous in one direction, but continuous rotation in one direction would require a rotary joint in the fluid path so that tubing 26 does not become twisted. The rotation can be around a horizontal axis. Preferably, the rotation is a total of 360° at a constant rate before reversing direction. A 180° rotation is generally sufficient if most of the time is spent at the extreme positions, and the time spent at the extremes is relatively equal. This mode of operation can be considered as turning bag 20 upside down periodically. Rotation around more than one axis can be useful, but will not typically be required.

One of the challenges with rotation of a simple bag is that the fluid outlet of a standard bag is at one edge. With this kind of a bag, when it is turned upside down, if there is any gross air in the bag, the air would be withdrawn rather than the fluid. This can be overcome in several ways. For example, one can expel the gross air so that only fluid with bubbles or particles remains. The bag can collapse as the fluid is withdrawn. Even when the bag is upside down, only fluid is withdrawn.

Figure 3B:
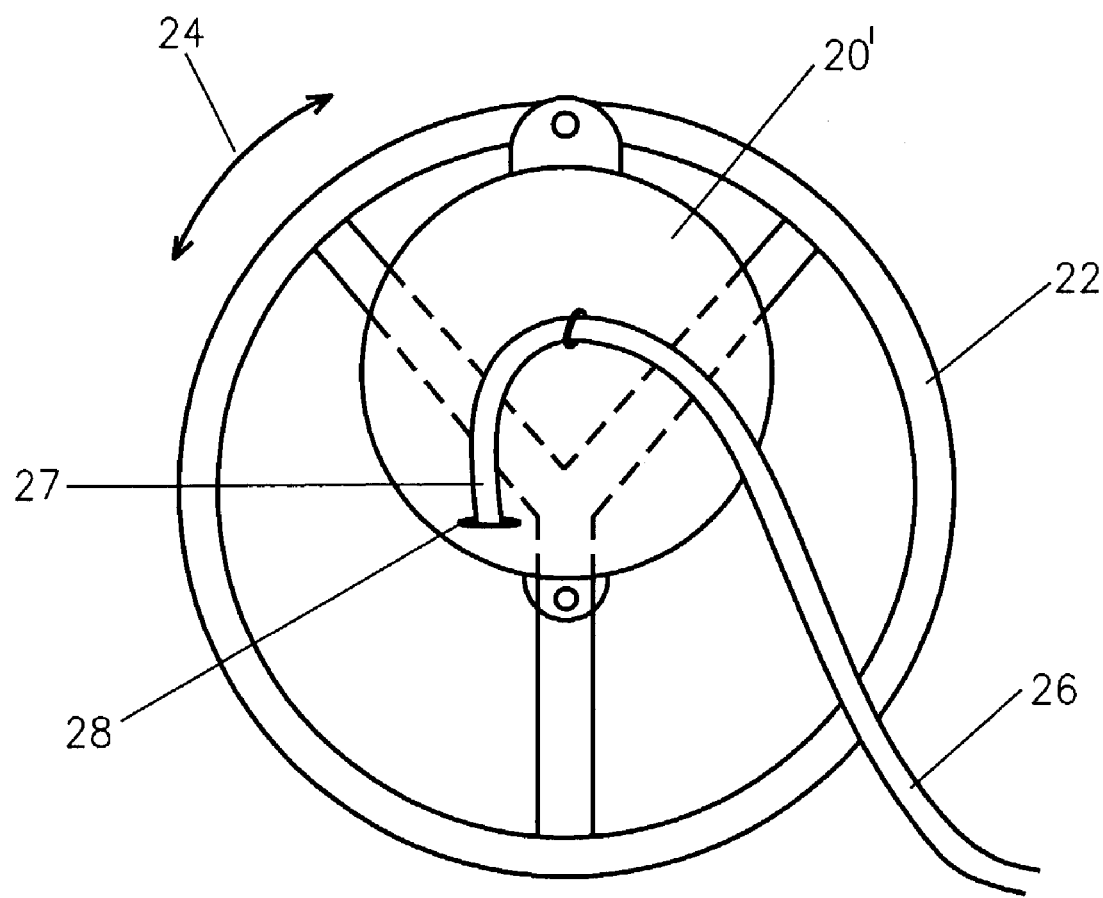
FIG. 3B illustrates an embodiment of a storage container for use with an agitation mechanism of the present invention.

A second method is illustrated in FIG. 3B. In this method, a rounded bag 20' preferably has an outlet tube 26 extending from the middle of bag 20'. Inside bag 20', connected to outlet tubing 26, there is a tube 27 with a weight 28 so that as bag 20' rotates, the open end of tube 27 stays in the fluid.

Figure 4:
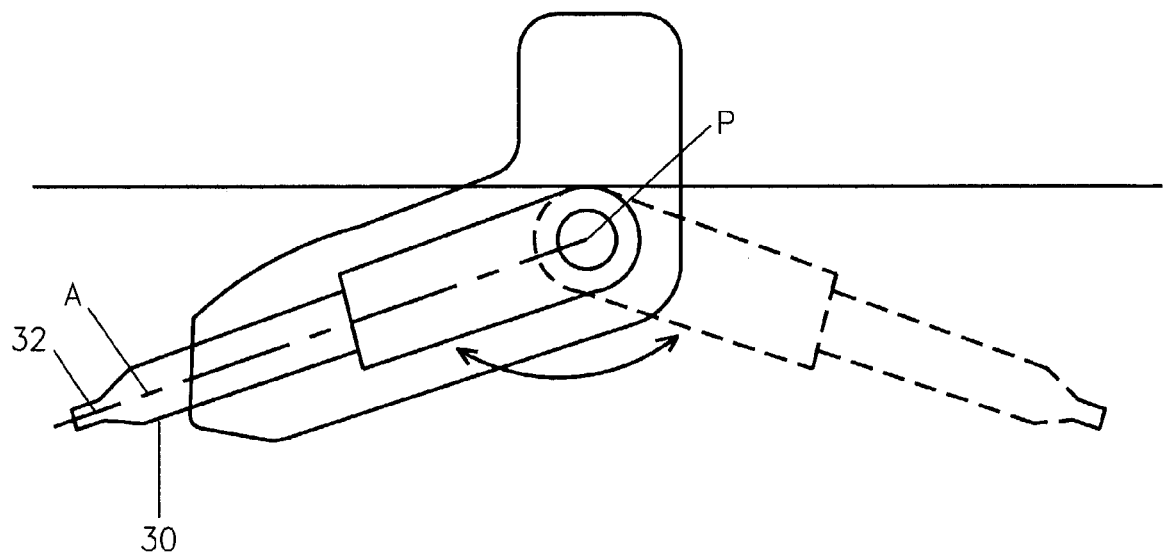
FIG. 4 illustrates an embodiment of an agitation mechanism for a syringe.

In the case of a syringe-based injector as illustrated in FIG. 4, turning syringe 30 on an axis perpendicular to longitudinal axis A of syringe barrel 32 will perform the desired mixing. This can also be considered as rotation of syringe barrel 32 about point P. In this case, the rotation is preferably slightly less than 180° so that gross or large bubbles cannot go to neck region 32 of syringe 30 and possibly be injected into the patient. As with the bag, it is preferable to expel all gross air before connecting the syringe to the fluid path to the patient.

Placement of a flow member 40 (see FIG. 3A), such as a sinker or float, inside the storage volume can increase mixing, particularly with a limited range of motion. The sinker or float tumbles, creating mixing, as the container is turned. Flow member 40 can be as simple as a weighted or hollow ball or disk in bag 20 of FIG. 3A. For a syringe, tilting the syringe past horizontal can cause a flow member to roll or float to the other end. It is desirable to have turbulence behind flow member 40 to achieve better mixing. In that regard, flow member 40 may be more effective as a disk with hole(s) in it, an airfoil, a flat spring, or an asymmetrical solid. The driving force for the motion of flow member 40 in this embodiment is gravity. It is also possible to drive the motion of a flow member within the contrast medium using energy other than the force of gravity (for example, magnetic fields or electromagnetic energy). Such embodiments will be discussed below.

Figure 5:
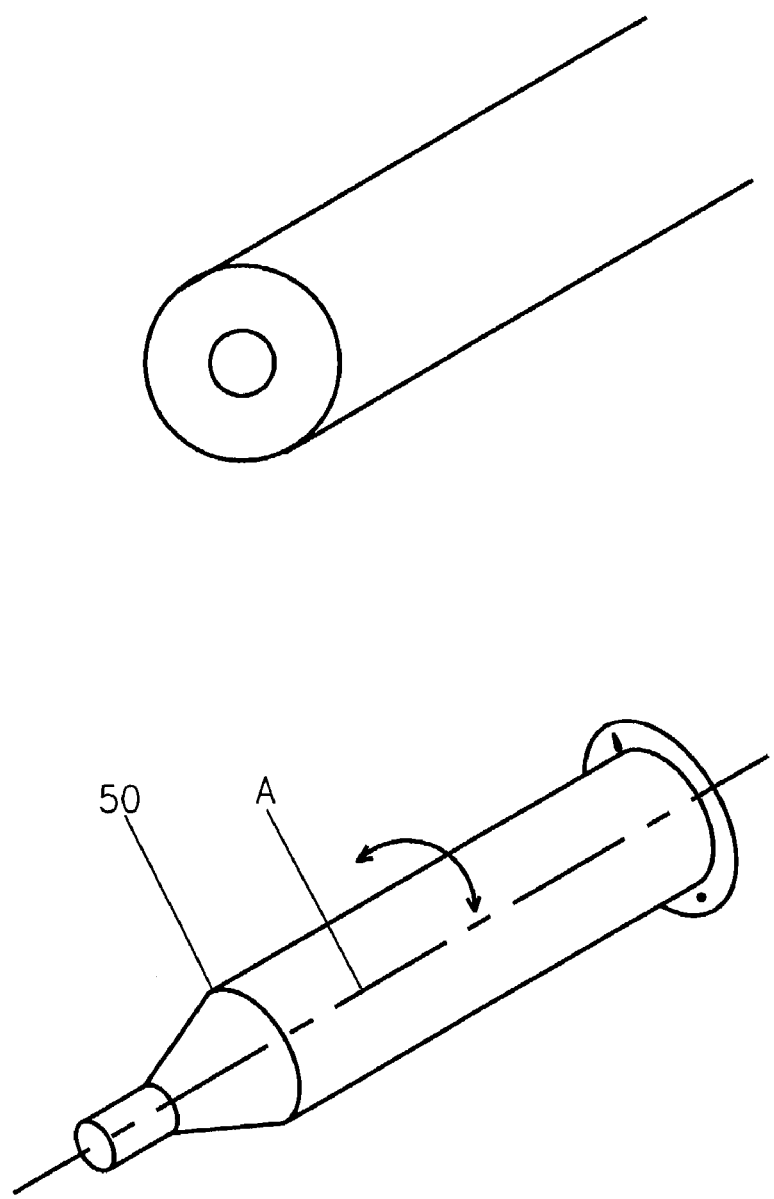
FIG. 5 illustrates an embodiment of an agitation mechanism for a syringe in which the syringe is rotated about its longitudinal axis.

A problem can occur in the case of rotational motion of the storage volume if the storage volume is relatively smooth and is rotationally symmetrical about the axis of rotation. The problem is that much of the volume of the fluid away from the walls will not rotate. To make matters worse, there are often some larger bubbles at the top of the storage volume, and these bubbles can cause the majority of the fluid to stay relatively fixed even if the storage volume container is rotated. This problem may occur, for example, if a syringe 50 is rotated about its longitudinal axis A, as illustrated in FIG. 5. For a syringe-based, powered injector system, however, rotating syringe 50 about its longitudinal axis A may be easier than rotating the entire motor and syringe assembly (see FIG. 4). If syringe 50 is to be rotated about its longitudinal axis A, it is preferable to disrupt or to destroy the rotational symmetry about longitudinal axis A to assist in forcing the fluid to rotate.

Figure 6:
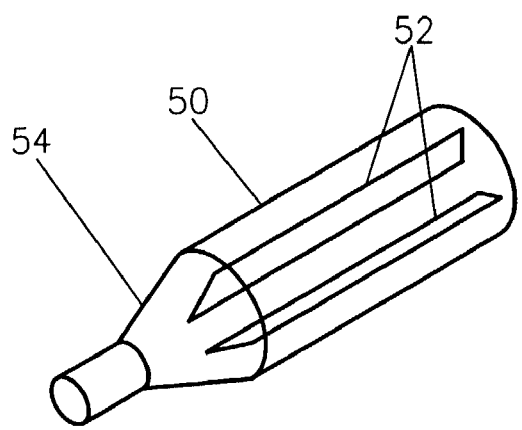
FIG. 6 illustrates the use of flow members within a syringe to overcome problems with symmetry about a rotational axis.

For example, the syringe can be formed to have a non-symmetrical (for example, an oval) cross section with respect to axis A. Because the pressures developed are relatively low, distortion and leakage under pressure during an injection is not a problem. In another embodiment, spokes or ribs 52 can be fixed upon the inside of syringe 50. Spokes or ribs 52 as illustrated in FIG. 6 can run the full length of the syringe neck and barrel. In this embodiment, corresponding slots would be formed in the plunger (not shown).

For simplicity of illustration, FIG. 6 illustrates a perspective view of two ribs 52 spaced about 90° apart. Four or more such ribs can be evenly spaced about the interior of the syringe barrel. Alternatively, ribs can be positioned just at the neck or tapered front section 54 of syringe 50. In this embodiment, a common solid plunger that stops just short of the ribs can be used. It is also possible that the ribs or spokes can protrude from the plunger itself. Such flow members can, for example, be made of the same rubber material as the plunger and arranged so that they collapse as the plunger impacts the front of the syringe. As the syringe rotates, the plunger rotates and the ribs cause the fluid to rotate.

Figure 7:
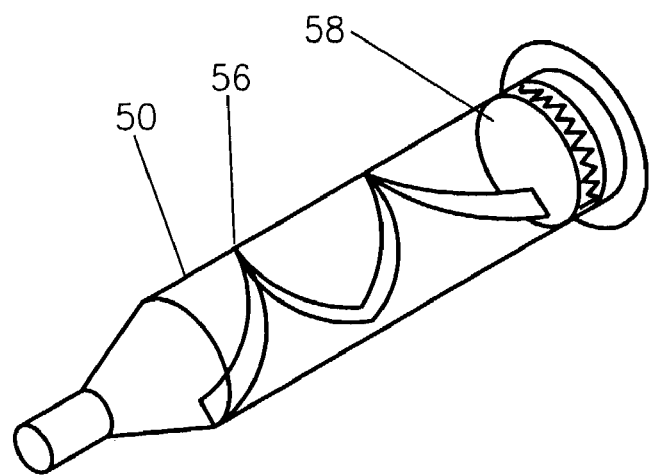
FIG. 7 illustrates another use of flow members within a syringe to overcome problems with symmetry about a rotational axis.

An alternative embodiment is to incorporate a collapsible flow member insert 56 (for example, a flat plastic spring) inside syringe 50, as illustrated in FIG. 7. Collapsible flow member 56 will rotate with syringe 50 or other container and will cause the fluid to be carried along as well. As plunger 58 moves forward, collapsible flow member 56 will be compressed.

Figure 8:
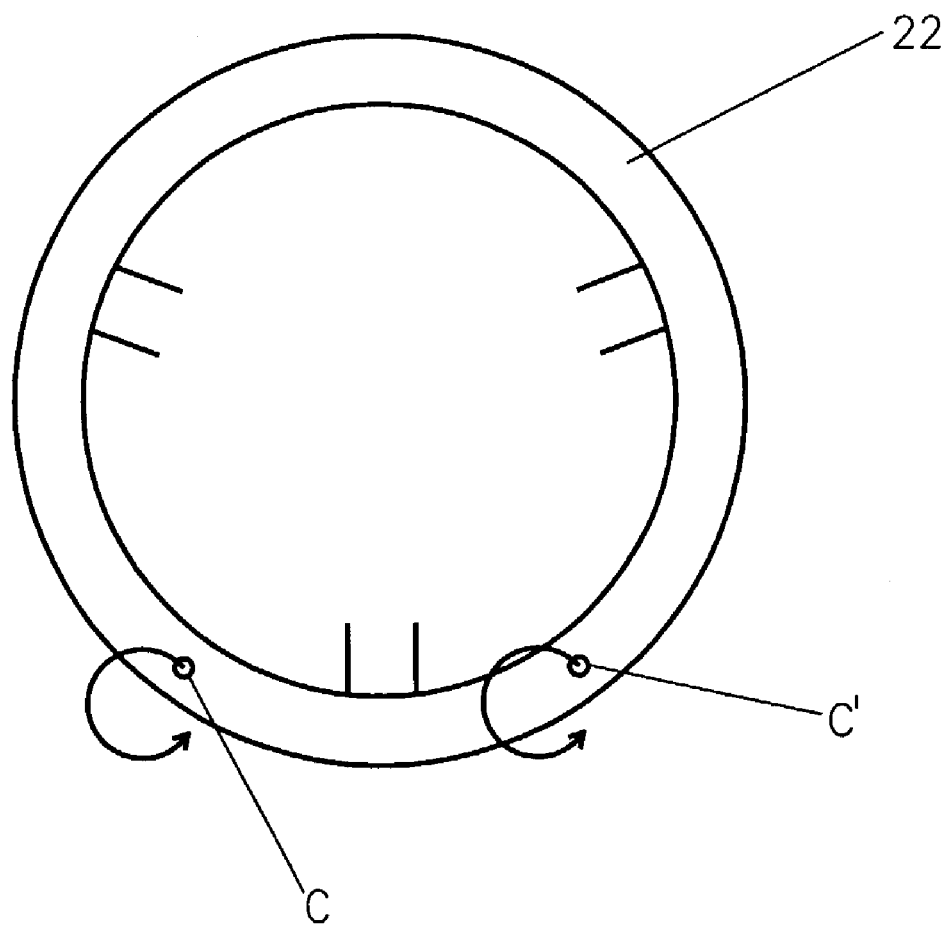
FIG. 8 illustrates a pattern of movement for a container to induce mixing within the container.

In another embodiment, the storage volume or container is moved in a manner other than rotation about an axis. For example, the storage volume can be shaken in a manner similar to the mixing of the contents of a can of paint through use, for example, of a motor or an electromagnetic coil and spring arrangement. FIG. 8 illustrates the same bag holder frame as shown in FIGS. 3A and 3B. In the embodiment of FIG. 8, however, bag holder 22 is moved so that point C follows the path indicated by the arrow adjacent thereto and point C' follows a corresponding path. Bag holder 22 is translated up, left, down, and then right. The cycle is then repeated. This motion will induce a mixing action in the fluid. As with other agitation mechanisms of the present invention, the mixing action is preferably sufficiently vigorous to adequately mix the fluid and keep the bubbles uniformly distributed without entraining large bubbles into the fluid.

A second category of agitation mechanisms or devices circulates the contrast medium within the storage volume without the requirement of bulk or gross movement of the storage volume. For example, a source of mechanical vibrational or ultrasonic energy can be used to introduce a streaming motion directly in the fluid. Moreover, because many of the contrast fluids are electrically conductive, electromagnetic fields may be induced within the fluid to cause the fluid to move or stream.

Furthermore, thermal convection currents can be induced in the contrast medium to mix the components thereof. In that regard, by heating at one side, one end or one section of the storage volume, thermal convection currents can be induced that gently move the fluid within the container. Indeed, it is generally more comfortable for the patient if the contrast medium is heated to approximately body temperature before injection.

The heating can be done by many methods. For example, a heater can be positioned on the outside of the container or an electromagnetic heating element can be placed within the fluid. A greater temperature difference can be created by heating one section of the storage volume and by cooling another section. A passive heat sink, for example, would create some cooling. A Peltier heater/cooler, which has no moving parts, can also be used. For example, the cold end of the heater/cooler can be positioned at one region of the storage volume and the warm end can be positioned at another. Because there is more heat output at the hot side than there is heat taken in at the cold side, fluid can be warmed above room temperature, which is desirable.

An energy source can also be used to create mechanical stirring within the storage volume. For example, mechanical vibration or ultrasonic energy can be used to induce a rotation of an insert (for example, an insert similar to that depicted in FIG. 7). Alternatively, a magnetic stirrer can be placed inside the storage volume and coupled to a moving magnet or magnetic field outside the storage volume. A standard magnetic stirrer, typically a small bar magnet coated with an inert plastic, can be used. The magnetic stirrer can also be made relatively thin with holes or vanes, so that it is pressed flat to the front of a syringe as the fluid is expelled. A magnetic stirrer for use in the present invention can be made to rotate or it can be translated. For example, the stirrer can be a relatively flat piece of material with a hole or holes in it that is moved back and forth along the long axis of a syringe. Alternatively, insert 56 of FIG. 7 can be made of a magnetic material and rotated inside syringe 50.

A mechanical stirring device can also be driven by a shaft that penetrates the storage volume or the tubing leading to or from the storage volume. For a bag or a bottle, the shaft can penetrate through a rubber seal. Bags can be made with several openings or seal sites along one edge. In the case of a flexible bag, the shaft can be rigidly sealed to the bag, and the bag flexed as the shaft is turned first one way and then the other. For a syringe, penetration is preferably through the center of the plunger or the outlet of the syringe. The plunger itself can have ribs as mentioned above and be rotated within a stationary syringe barrel.

Figure 9:
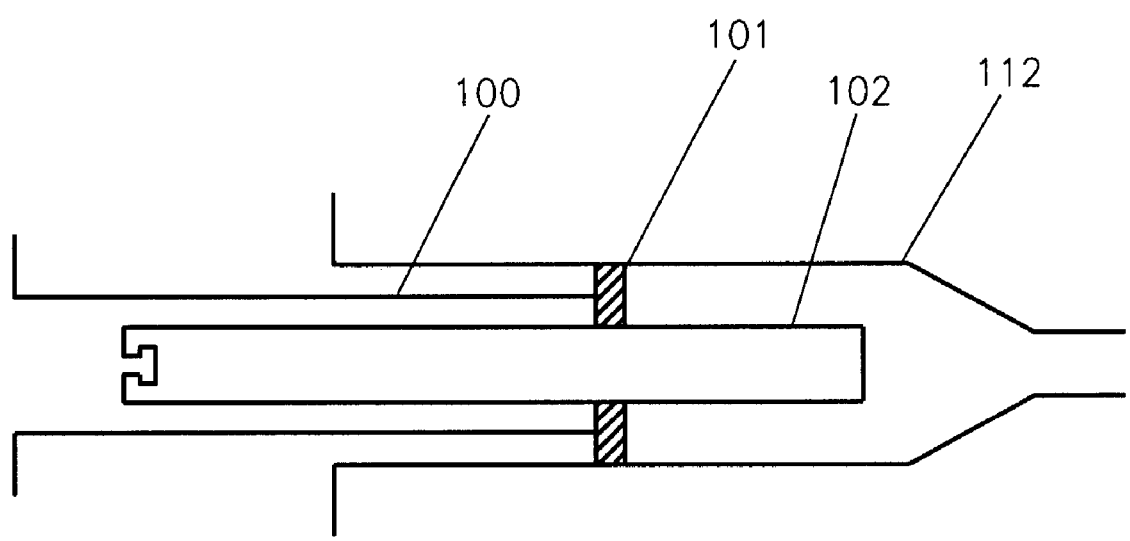
FIG. 9 illustrates an embodiment of a syringe having an internal agitation mechanism.

Mechanical mixing can also be effected through use of a multi-component plunger. In the embodiment of FIG. 9, for example, the plunger has two parts or components 101, 102 that can be moved separately forward and rearward in syringe barrel 112. Sealing component 101 is preferably an elastomeric piece that is attached to drive member 100. Sealing component 101 provides a seal between a center component 102 and the syringe barrel 112. For sealing simplicity, it is best if sealing component 101 is cylindrically symmetrical about the center axis of syringe barrel 112.

By moving center component 102 rearward while sealing component 101 is moved forward (that is, toward the tip or open end of syringe barrel 112), the fluid is circulated within syringe barrel 112. Subsequently, sealing component 101 is moved forward while center component 102 is withdrawn. If the cross-sectional areas of sealing component 101 and center component 102 are equal, equal volumes are displaced for equal linear motions. To pressurize and inject fluid, one component of the plunger is moved forward more than the other is moved rearward. Clearly, sealing component 101 should never go farther forward than the forward end of center component 102, otherwise fluid will escape. The forward end of center component 102 could be enlarged in radius to prevent this result.

If the storage volume is a collapsible or compressible container, such as a bag, a counterpart to the multi-component plunger discussed above is to provide a mechanism that compresses segments of the bag, pushing fluid from one part of the bag into another. This result can be achieved by having two plates that push on alternate sides (for example, top/bottom or left/right) of the bag. One side of the bag does not need to be totally compressed, and fluid can be drawn from the bag and injected into the patient while the agitation is continuing.

Alternatively, a roller or other compression member can move over the surface of a compressible or collapsible bag. As the roller moves, the contrast medium is agitated within the storage volume.

Movement of the fluid in the storage container can also be induced by bubbling a sterile gas through the container. As the bubbles rise, they create currents in the fluid that accomplish the mixing. In one embodiment, the gas enters the container from outside the container. In this case, the gas preferably is passed through a sterile filter. Preferably, there is also a sterile vent communicating with the top of the storage container to let the gas out and prevent a buildup of pressure. The gas can also be pumped out of the top of the storage volume and returned into the bottom of the storage volume by, for example, a peristaltic pump.

Figure 10:
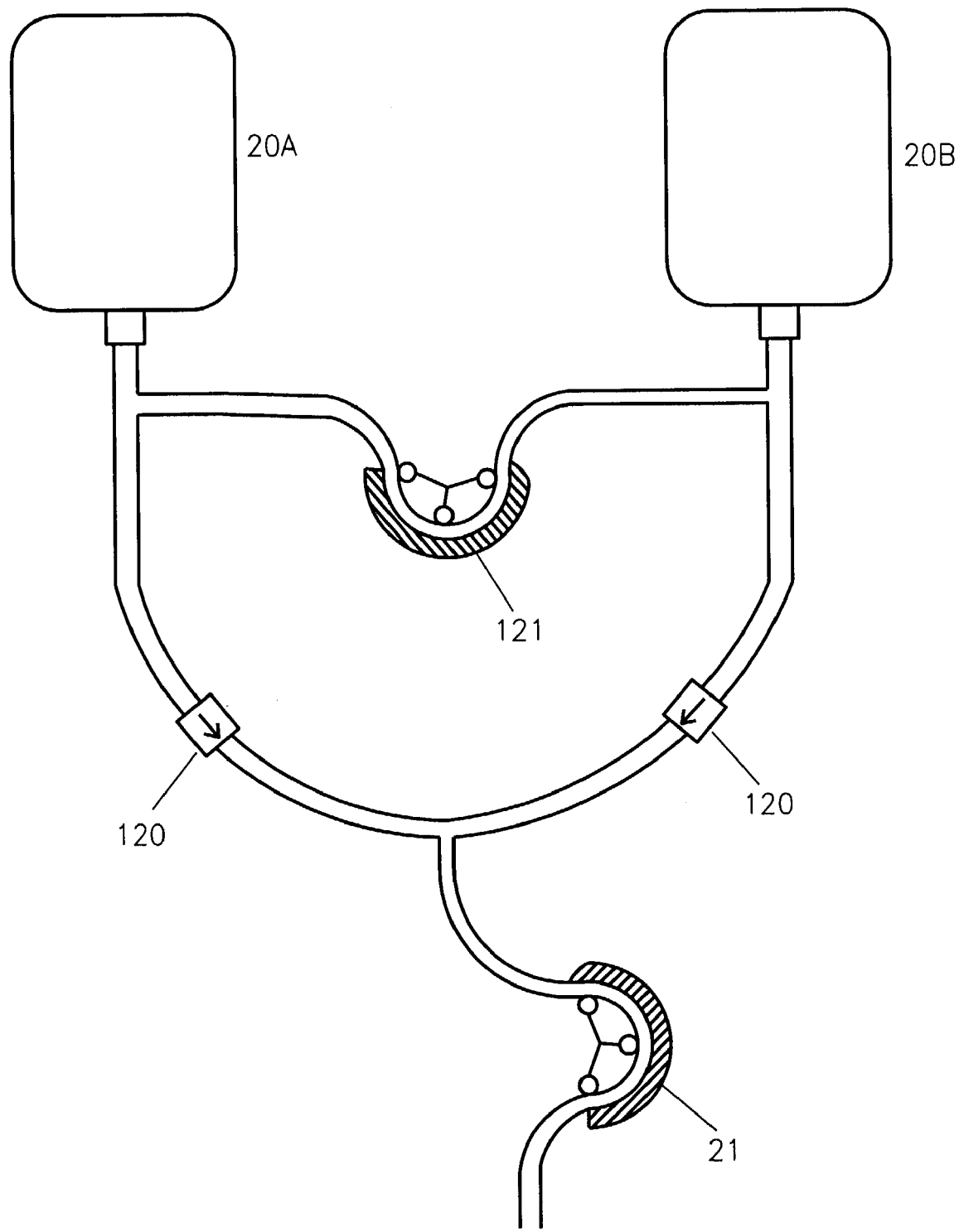
FIG. 10 illustrates an embodiment of a multi-container agitation mechanism.

A third category of agitation devices of the present invention operates by circulating the contrast medium with a pump or similar device. For example, the contrast medium can be pumped between two storage volumes or from the one storage volume, through an external fluid path segment, and back into the storage volume at a different point. The simplest embodiment uses two collapsible bags 20a and 20b, as illustrated in FIG. 10.

A first pump 21 (for example, a peristaltic pump) pressurizes the contrast medium for injection. A second pump 121 (for example, a peristaltic pump) moves fluid from one bag into the other at a rate sufficient to keep the particles (that is, bubbles or solid particles) suspended in the liquid contrast medium. One-way valves 120 preferably keep the fluid from simply moving around the fluid path without entering bags 20a and 20b. In this embodiment, pump 121 moves the fluid both ways. Glass bottles with air above the fluid (i.e., head space) can also be used as storage volumes.

Figure 11:
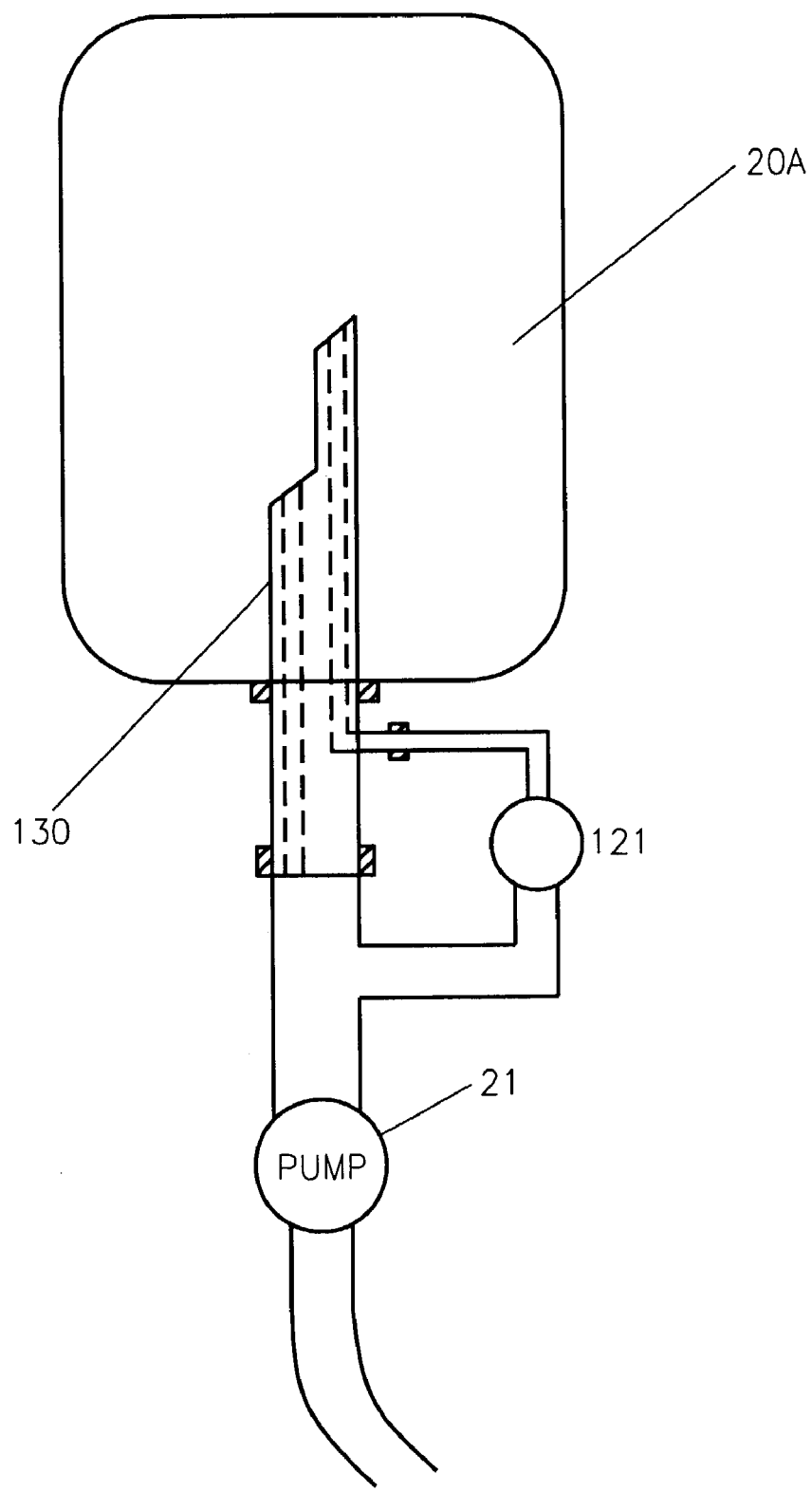
FIG. 11 illustrates the use of an agitation pump to induce mixing within a container.

Alternatively, pump 121 can pump the contrast medium out of the bottom of container 20a and push it into the top of container 20a, as illustrated in FIG. 11. With a bottle or bag, this can be done through a single, multiple-lumen spike 130. The same result can be accomplished with a syringe as well, but is not as advantageous because a second pump is required. A different pump 21 (as illustrated in FIGS. 10 and 11) or an active valve arrangement that stops circulation during injection can be used to inject the fluid into the patient.

Figure 12:
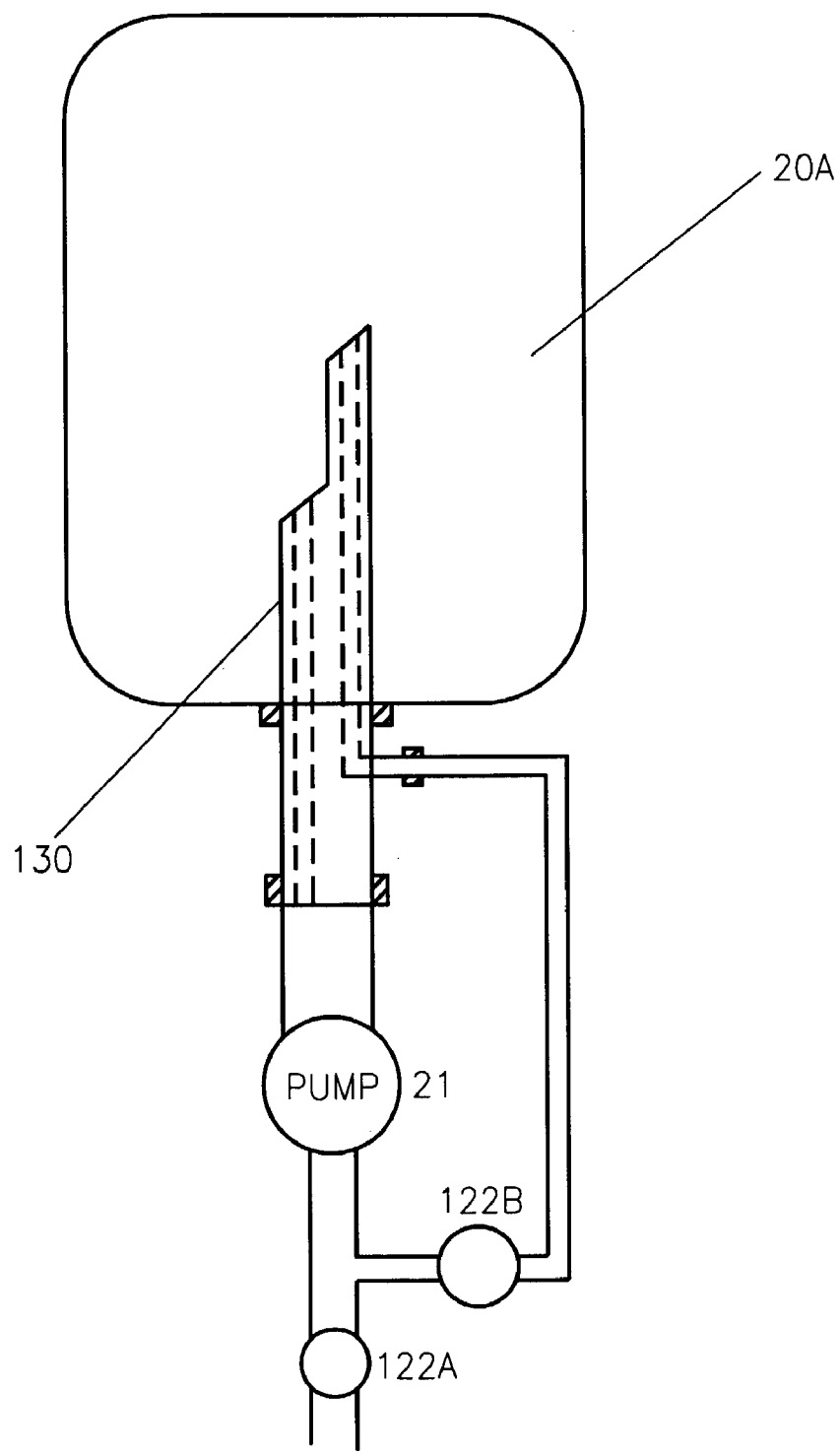
FIG. 12 illustrates the use of a common pump to induce mixing within a fluid and to pressurize the fluid for injection.

In that regard, FIG. 12 shows an embodiment including a single pump 21 and an active valve arrangement that stops circulation during injection to inject the fluid into the patient. Valve 122a is closed and valve 122b is open to circulate fluid to agitate the particles. Valve 122a is opened and valve 122b is closed to inject fluid into the patient. While this embodiment is simpler than the embodiment of FIG. 11 in that it requires only one pump, it has the disadvantage that agitation cannot be continued while contrast medium is being continually injected into the patient. By rapidly switching between valve 122a being open and 122b being open, it is possible for pump 21 to alternately inject fluid into the patient and circulate fluid into the volume to provide agitation.

Figure 13:
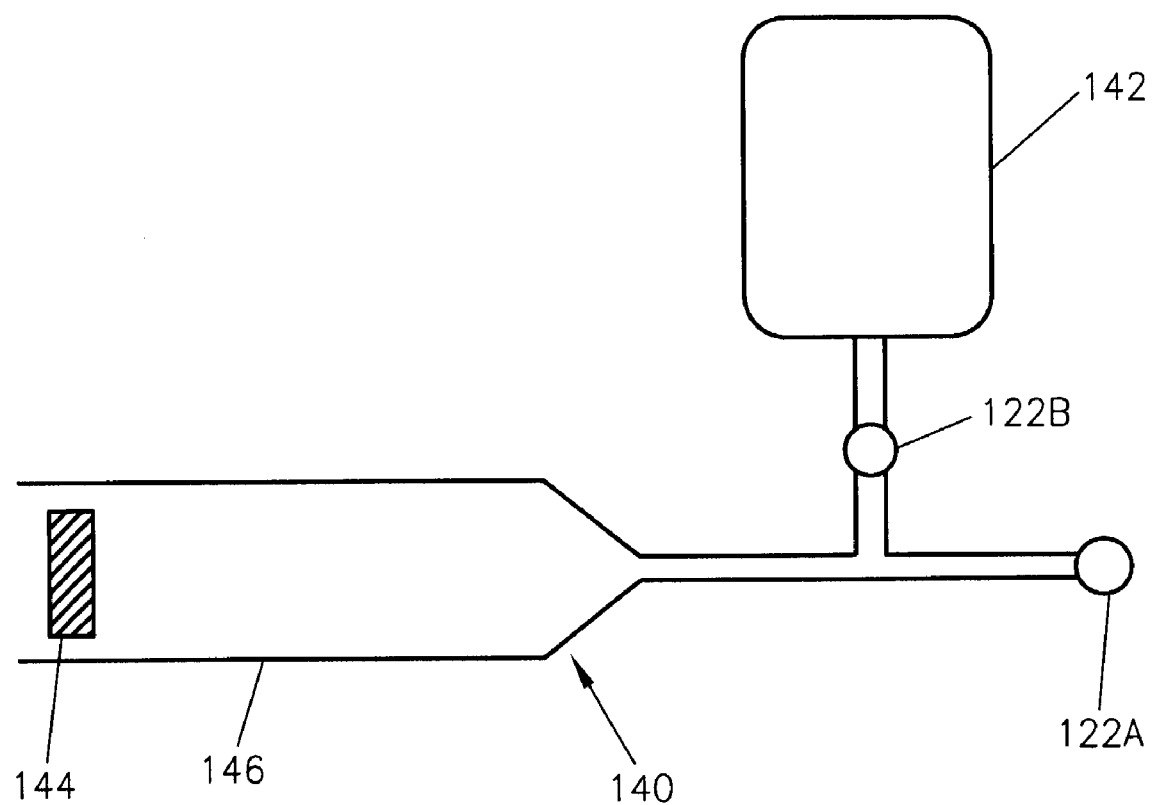
FIG. 13 illustrates the use of a syringe to induce mixing within a fluid and to pressurize the fluid for injection.

FIG. 13 illustrates a syringe-based system in which a syringe 140 ejects the fluid into a container 142, such as a collapsible bag (or glass bottle with a head space), which is preferably positioned at a higher elevation than syringe 140. When enough fluid is ejected, syringe plunger 144 is reversed and pulls fluid back into syringe barrel 146. This embodiment has the benefit that only one motor is required. Valves 122a and 122b direct the fluid to the patient or to the storage volume 142. A potential shortcoming of this arrangement is that agitation cannot take place while fluid is being continuously injected into the patient.

Figure 14:
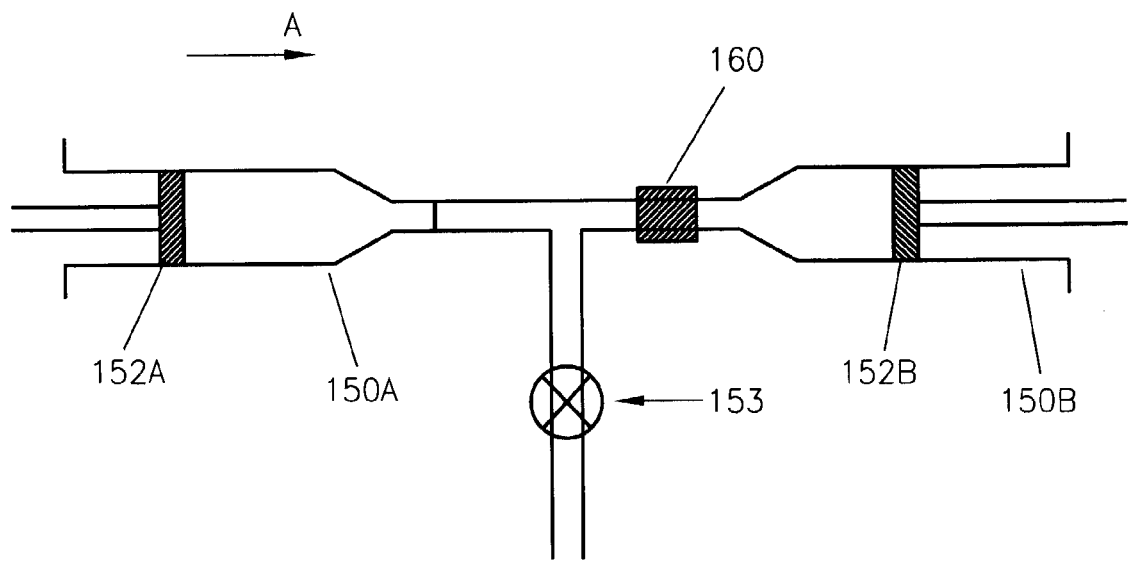
FIG. 14 illustrates the use of multiple syringes for mixing and injection.

FIG. 14 illustrates an embodiment of an injection system comprising two syringes 150a and 150b. For agitation, one of syringe plungers 152a and 152b moves in one direction (see Arrow A) to draw fluid inward while the other moves in the same direction (Arrow A) to expel fluid. The motion of plungers 152a and 152b can be coupled to accomplish this result. Syringes 150a and 150b can be positioned end-to-end as shown in FIG. 14, or they could be side-by-side as illustrated in FIGS. 15A and 15B.

Figure 15A:
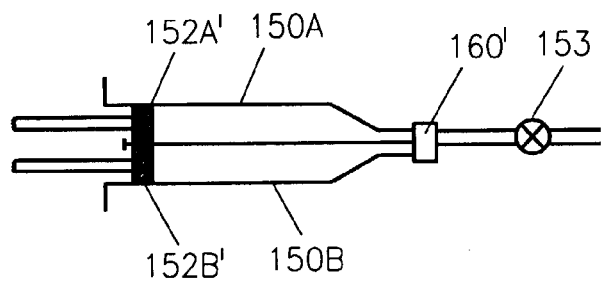
FIGS. 15A and 15B illustrate the use of two syringes in a side-by-side arrangement for use in mixing and injection.
Figure 15B:
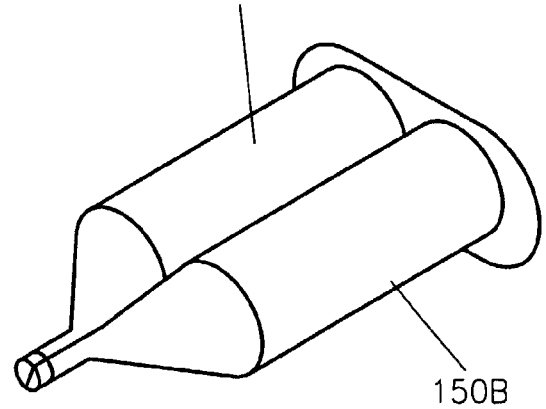

In the embodiment of FIGS. 15A and 15B, it is difficult to mechanically couple the motions of plungers 152a' and 152b' during use because they must move in opposite directions to move the fluid from one syringe to the other. A two-motor embodiment has the benefit that the contrast medium can be agitated while the fluid is being injected. The fluid rate or volume injected into the patient is the net difference between the amount one syringe piston moves forward to inject fluid and the amount the second syringe piston moves back to draw in fluid. Valve 153 operates to ensure that there is no unintentional injection of fluid into the patient. If the motion is controlled with sufficient accuracy, valve 153 is not required.

If the mixing is not sufficient for certain contrast media, a static vane mixer or other mixing element can be incorporated into the fluid path between the two storage volumes. This is indicated by fluid path element 160 in FIG. 14 and 160' in FIG. 15A. (If this enhanced mixing is not needed, then 160 and 160' are simply open fluid paths.) A fluid path element to enhance mixing can be incorporated in any of the previous systems which use a pressurizing device or pump to move the fluid.

All of the above agitation mechanisms have been discussed primarily in relation to agitation of an ultrasound contrast medium once it has been prepared. For many contrast mediums, such preparation includes mixing a powder with a liquid and vigorously mixing or agitating the mixture to create a suspension of the small particles (bubbles or solids) in a liquid, which serves to scatter ultrasound energy. All of the above embodiments of the present invention are applicable to provide injector-based initial mixing of the contrast medium. It may, however, be desirable to more vigorously mix the contrast medium to initially create a suspension and then to maintain such a suspension. In that regard, the agitation devices of the present invention are preferably operable at two or more levels or speeds. For example, a first, more vigorous level of agitation can be used in initial preparation of a medium. A second, less vigorous level of agitation can be used to maintain a suspension or mixing within the medium. The level of agitation and other aspects of the agitation mechanisms of the present invention are easily controlled via a controller (such as controller 4) as illustrated in FIG. 1. Such a controller preferably comprises a microprocessor.

A static vane mixer or another type of shear inducing mechanical structure may be used to ensure good dispersion in initial preparation of medium. Other manners of inducing vigorous mixing include creating areas of induced turbulence or fluid flow impingement through, for example, use of a gear pump with designed-in "blow by" and/or rotary flow elements or use of balls that circulate in the flow causing turbulence and improving mixing.

Some contrast media require specific sequences of pressures to create microbubbles. One type involves a liquid that, when subjected to decreased pressures, boils to create relatively stable microbubbles. The embodiments involving relatively rigid containers, such as syringes or bottles, can be used to activate this type of contrast media by creating a sufficient negative pressure. The embodiment of FIG. 13 is especially advantageous because volumes of contrast media can be activated just before they are to be injected. It is theoretically possible to use all of the embodiments listed herein if the agitation is vigorous enough to create turbulence, because turbulent flow can create regions of negative pressure in vortices.

Due to the need to separately package the two components of most contrast media for ultrasound, the preferred embodiments of the present invention for initial mixing of contrast media are those that comprise two storage volumes. One storage volume can hold the powder and the other storage volume can hold the liquid. When the components are to be mixed, a fluid path is preferably created between the two volumes by breaking seals and/or adding tubing. The liquid is then injected into the storage volume containing the powder. Subsequently, the mixture is vigorously moved from one volume to the other. After a number of cycles as determined by time, operator observation, or some measured parameter such as optical density or sound transmission, any large bubbles or gas can be removed and the agitation can be reduced to the level needed to maintain suspension of the particles.

Figure 16:
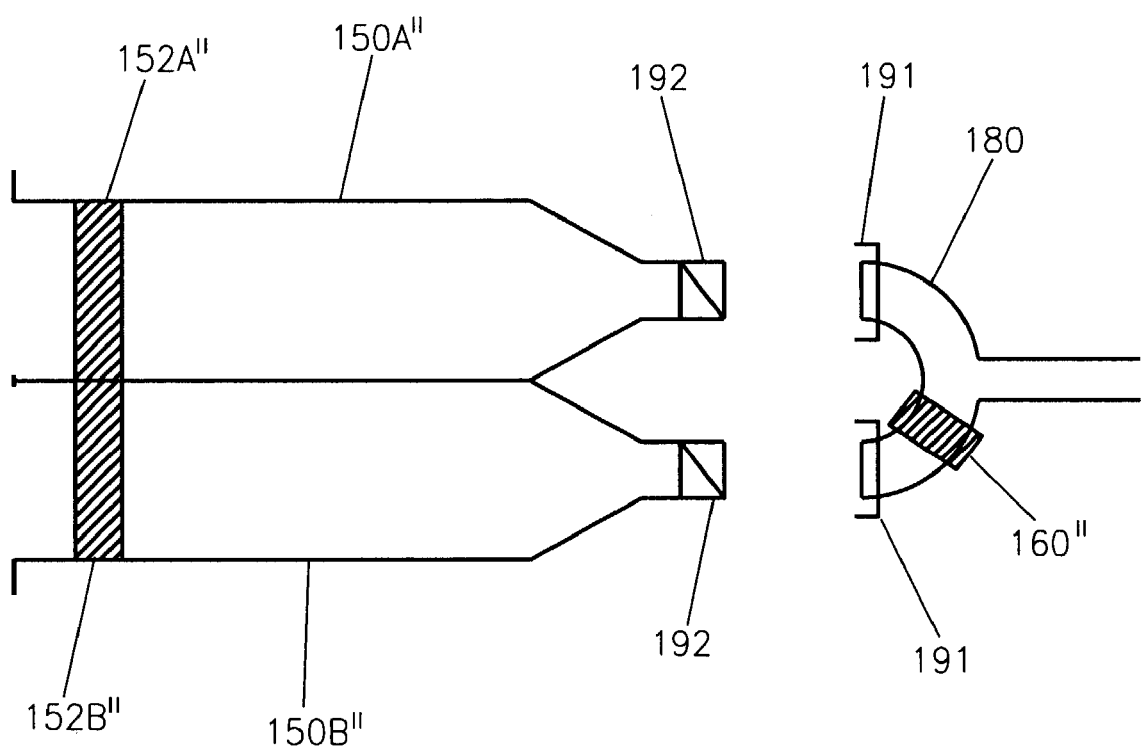
FIG. 16 illustrates the use of two syringes in a side-by-side arrangement wherein each syringe has a separate outlet.

The side-by-side syringes of FIGS. 15A and 15B are especially advantageous for storage, shipping and subsequent mixing. For example, one syringe can hold a powder, and the other syringe can hold a liquid. After placing the syringes into the injector, the seals for each syringe can be broken and a fluid path element put in place that allows fluid flow from one chamber to the other. Each syringe outlet can have an individual standard Luer connector 192, as illustrated in FIG. 16. Swivel nuts 191 can be used to secure the fluid path element 180 to the Luer connectors 192.

As mentioned above, a fluid path element 160" (see FIG. 16) may be included to increase the agitation or mixing as the media is moved through it. Alternatively, the two syringes may share the lumen of a single Luer connector, as is shown in FIG. 15B.

The syringes can be initially sealed by a Luer connector with two extensions to seal the lumens. The fluid path element can be simply a Luer cap with an open inside so that fluid can move between the two syringes. For injection, the cap can be replaced by tubing connectable to the patient. Alternately, the embodiment of FIG. 15A can be used.

It is also possible to provide a package with two separate syringes that can be placed side by side in the injector and connected via a fluid path to operate, as shown in FIG. 15A. It is most convenient for the operator if the syringes are one piece, but that is not essential to gain the benefits of this invention.

In another embodiment, one component of the medium comes in a syringe and a second component comes in a bottle or a bag. This would be a preferable packaging method for use with the embodiment shown in FIG. 13. The two components could also both come packaged in bags for use with the embodiment shown in FIG. 10.

In all the possible arrangements of packaging the various components, it is a benefit to the operator if some or all of the elements of the fluid path are preconnected to reduce the amount of work for the operator. This also has the benefit of reducing the possibility of operator error as well.

While the present invention has been discussed in connection with the delivery of a fluid with suspended particles to a patient for use as an ultrasound contrast medium, there are many other uses for the present invention. For example, the agitation mechanisms, systems and methods of the present invention can be used in connection with powdered medications that are difficult to dissolve or that simply need to be stored in a powder form to preserve their potency. The controlled vigorous agitation provided by the present invention will speed dissolution. In some of these applications, automated mixing is all that is needed, because the powder dissolves in the liquid and once dissolved, no further agitation is needed. Moreover, the agitation mechanisms and methods of the present invention are also suitable for use in non-medical applications wherein mixing is desirable.

Although the present invention has been described in detail in connection with the above embodiments and/or examples, it is to be understood that such detail is solely for that purpose and that variations can be made by those skilled in the art without departing from the spirit of the invention. The scope of the invention is indicated by the following claims, rather than by the foregoing description. All changes or modifications which come within the meaning and range of equivalency of the claims are to be embraced within their scope.

What is claimed is:

1. A system for injection of a multi-component medium into a patient, the system comprising:
   at least a first container to hold the medium;
   a pressurizing mechanism for pressurizing the medium for injection into the patient;
   a patient fluid path in operative connection with the pressurizing mechanism, the fluid path terminating in a patient connector;
   a fluid path for conducting medium from the at least a first container to the pressurizing mechanism; and
   an agitation mechanism to circulate at least a portion of the medium to maintain the components of the medium in a mixed state for injection of the medium into the patient.

2. The system of claim 1, further comprising a second container and a fluid path element to the second container, and wherein the agitation mechanism moves at least a portion of the medium between the first container and the second container.

3. The system of claim 2 wherein the medium is moved between the first container and the second container in an alternating fashion.

4. The system of claim 1 wherein the agitation mechanism and the pressurizing mechanism are the same and the system further comprises a valve system to control injection of the medium and agitating circulation of the medium.

5. The system of claim 4 wherein the valve system comprises a valve.

6. The system of claim 5 wherein the valve is a one-way valve.

7. The system of claim 1 wherein the agitation mechanism is a peristaltic pump.

8. The system of claim 1 wherein the pressurizing mechanism is a peristaltic pump.

9. A system for injection of a multi-component medium into a patient, the system comprising:
   at least a first container to hold the medium;
   a pressurizing mechanism for pressurizing the medium for injection into the patient;
   a fluid path for conducting medium from the at least a first container to the pressurizing mechanism;
   an agitation mechanism to circulate at least a portion of the medium to maintain the components of the medium in a mixed state for injection of the medium into the patient; and
   a second container and a fluid path element to the second container, wherein the agitation mechanism moves at least a portion of the medium between the first container and the second container;
   wherein a first valve is disposed within the fluid path and a second valve is disposed within the fluid path element to the second container.

10. The system of claim 9 wherein the first and second valves are one-way valves.

11. A system comprising:
    a first container for holding a medium;
    a second container for holding a medium;
    a first fluid path containing a first valve disposed between the first container and a pressurizing mechanism;
    a second fluid path containing a second valve disposed between the second container and the pressurizing mechanism;
    a third fluid path disposed between the first fluid path and the second fluid path;
    an agitation mechanism associated with the third fluid path and adapted to circulate at least a portion of the medium; and
    a pressurizing mechanism associated with the first and second fluid paths for pressurizing the medium.

12. The system of claim 11 wherein the first and second valves are one-way valves.

13. The system of claim 11 wherein the agitation mechanism is a peristaltic pump.

14. The system of claim 11 wherein the pressurizing mechanism is a peristaltic pump.

15. A system for injection of a multi-component medium, the system comprising:
    at least a first container to hold the medium;
    a pressurizing mechanism for pressurizing the medium;
    a fluid path for conducting medium from the at least a first container to the pressurizing mechanism;
    a first valve disposed within the fluid path;
    a second container;
    a fluid path element to the second container, and
    a second valve disposed within the fluid path element to the second container; and
    an agitation mechanism to circulate at least a portion of the medium to maintain the components of the medium in a mixed state, wherein the agitation mechanism moves at least a portion of the medium between the first container and the second container.

16. The system of claim 15 wherein the first and second valves are one-way valves.

* * * * *